(12) United States Patent
Gross et al.

(10) Patent No.: US 7,778,703 B2
(45) Date of Patent: *Aug. 17, 2010

(54) SELECTIVE NERVE FIBER STIMULATION FOR TREATING HEART CONDITIONS

(75) Inventors: Yossi Gross, Moshav Mazor (IL); Shai Ayal, Jerusalem (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1266 days.

This patent is subject to a terminal disclaimer.

(21) Appl. No.: 10/205,475

(22) Filed: Jul. 24, 2002

(65) Prior Publication Data
US 2003/0045909 A1 Mar. 6, 2003

Related U.S. Application Data

(63) Continuation-in-part of application No. PCT/IL02/00068, filed on Jan. 23, 2002, which is a continuation-in-part of application No. 09/944,913, filed on Aug. 31, 2001, now Pat. No. 6,684,105.

(60) Provisional application No. 60/383,157, filed on May 23, 2002.

(51) Int. Cl.
 *A61N 1/00* (2006.01)
(52) U.S. Cl. ............... 607/9; 607/62; 607/118
(58) Field of Classification Search ........ 607/1, 607/2, 38–41, 46, 48–49, 74, 116–118, 9, 607/62
See application file for complete search history.

(56) References Cited

U.S. PATENT DOCUMENTS 3,411,507 A 11/1968 Wingrove .......... 128/422
4,019,518 A 4/1977 Maurer et al.

(Continued)

FOREIGN PATENT DOCUMENTS

EP 0 688 577 A1 12/1995

(Continued)

OTHER PUBLICATIONS

Jones et al. "Heart rete responses to selective stimulation of cardiac vagal c fibres in anaesthetized cats, rats and rabbits", Journal Physiology 1995; 489;203-214.*

(Continued)

*Primary Examiner*—Mark W Bockelman
(74) *Attorney, Agent, or Firm*—John P. White; Cooper & Dunham LLP

(57) ABSTRACT

Apparatus for treating a heart condition of a subject is provided, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

22 Claims, 4 Drawing Sheets

U.S. PATENT DOCUMENTS

| | | |
|---|---|---|
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | Van Den Honert ......... 128/746 |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. .............. 128/784 |
| 4,608,985 A | 9/1986 | Crish et al. ............. 128/419 R |
| 4,628,942 A | 12/1986 | Sweeney et al. ........... 128/784 |
| 4,632,116 A | 12/1986 | Rosen et al. |
| 4,649,936 A | 3/1987 | Ungar et al. ............... 128/784 |
| 4,663,102 A | 5/1987 | Brenman et al. |
| 4,702,254 A | 10/1987 | Zabara ...................... 128/421 |
| 4,739,764 A | 4/1988 | Lue et al. ................ 128/419 R |
| 4,867,164 A | 9/1989 | Zabara ...................... 128/421 |
| 4,926,865 A | 5/1990 | Oman |
| 4,962,751 A | 10/1990 | Krauter ........................ 128/ 4 |
| 5,025,807 A | 6/1991 | Zabara ...................... 128/421 |
| 5,042,497 A | 8/1991 | Shapland |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke et al. ........ 128/419 R |
| 5,199,428 A | 4/1993 | Obel et al. |
| 5,199,430 A | 4/1993 | Fang et al. .............. 128/419 E |
| 5,203,326 A | 4/1993 | Collins |
| 5,205,285 A | 4/1993 | Baker ..................... 128/423 R |
| 5,215,086 A | 6/1993 | Terry et al. ................. 128/421 |
| 5,224,491 A | 7/1993 | Mehra |
| 5,251,621 A | 10/1993 | Collins |
| 5,263,480 A | 11/1993 | Wernicke et al. ............ 607/118 |
| 5,282,468 A | 2/1994 | Klepinski ................... 128/642 |
| 5,292,344 A | 3/1994 | Douglas ...................... 607/40 |
| 5,299,569 A | 4/1994 | Wernicke et al. ............. 607/45 |
| 5,314,495 A | 5/1994 | Kovacs |
| 5,330,507 A | 7/1994 | Schwartz |
| 5,335,657 A | 8/1994 | Terry et al. ................... 607/45 |
| 5,411,531 A | 5/1995 | Hill et al. |
| 5,423,872 A | 6/1995 | Cigaina ....................... 607/40 |
| 5,437,285 A | 8/1995 | Verrier et al. |
| 5,439,938 A | 8/1995 | Snyder et al. |
| 5,454,840 A | 10/1995 | Krakovsky et al. |
| 5,507,784 A | 4/1996 | Hill et al. |
| 5,540,730 A | 7/1996 | Terry, Jr. et al. ............... 607/40 |
| 5,540,734 A | 7/1996 | Zabara |
| 5,562,718 A | 10/1996 | Palermo |
| 5,571,150 A | 11/1996 | Wernicke et al. ............. 607/72 |
| 5,578,061 A | 11/1996 | Stroetmann et al. |
| 5,602,301 A | 2/1997 | Field |
| 5,634,462 A | 6/1997 | Tyler et al. |
| 5,645,570 A | 7/1997 | Corbucci et al. |
| 5,690,681 A | 11/1997 | Geddes et al. |
| 5,690,691 A | 11/1997 | Chen ........................... 607/40 |
| 5,700,282 A | 12/1997 | Zabara |
| 5,707,400 A | 1/1998 | Terry et al. ................... 607/44 |
| 5,711,316 A | 1/1998 | Elsberry et al. |
| 5,716,385 A | 2/1998 | Mittal et al. .................. 607/40 |
| 5,755,750 A | 5/1998 | Petruska et al. ............... 607/75 |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois .................... 607/40 |
| 5,916,239 A | 6/1999 | Geddes et al. |
| 5,938,584 A | 8/1999 | Ardito et al. |
| 6,026,326 A | 2/2000 | Bardy ......................... 607/40 |
| 6,038,476 A | 3/2000 | Schwartz |
| 6,058,331 A | 5/2000 | King |
| 6,066,163 A | 5/2000 | John |
| 6,073,048 A | 6/2000 | Kieval et al. |
| 6,083,249 A | 7/2000 | Familoni ..................... 607/40 |
| 6,086,525 A | 7/2000 | Davey et al. |
| 6,091,977 A | 7/2000 | Tarjan et al. |
| 6,091,992 A | 7/2000 | Bourgeois ................... 399/297 |
| 6,094,598 A | 7/2000 | Elsberry et al. |
| 6,097,984 A | 8/2000 | Douglas ....................... 607/40 |
| 6,104,955 A | 8/2000 | Bourgeois ................... 607/40 |
| 6,104,960 A | 8/2000 | Duysens et al. |
| 6,119,516 A | 9/2000 | Hock |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja ........................ 607/45 |
| 6,230,061 B1 | 5/2001 | Hartung |
| 6,240,314 B1 | 5/2001 | Plicchi et al. |
| 6,266,564 B1 | 7/2001 | Hill |
| 6,272,377 B1 | 8/2001 | Sweeney et al. |
| 6,319,241 B1 | 11/2001 | King et al. ................... 604/502 |
| 6,341,236 B1 | 1/2002 | Osorio |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,449,507 B1 | 9/2002 | Hill et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,542,774 B2 | 4/2003 | Hill et al. |
| 6,564,096 B2 | 5/2003 | Mest |
| 6,587,727 B2 | 7/2003 | Osorio et al. |
| 6,610,713 B2 | 8/2003 | Tracey |
| 6,622,041 B2 * | 9/2003 | Terry et al. ................... 607/9 |
| 6,628,987 B1 | 9/2003 | Hill et al. |
| 6,668,191 B1 | 12/2003 | Boveja |
| 6,671,556 B2 | 12/2003 | Osorio et al. |
| RE38,705 E | 2/2005 | Hill et al. |
| 6,865,416 B2 | 3/2005 | Dev et al. |
| 6,885,888 B2 | 4/2005 | Rezai |
| 6,895,280 B2 | 5/2005 | Meadows et al. |
| 6,907,293 B2 | 6/2005 | Grill et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 * | 7/2006 | Boveja et al. .................. 607/45 |
| 7,123,961 B1 | 10/2006 | Kroll et al. |
| 7,142,917 B2 | 11/2006 | Fukui |
| 7,509,166 B2 | 3/2009 | Libbus et al. |
| 7,623,926 B2 | 11/2009 | Rossing et al. |
| 2002/0035335 A1 | 3/2002 | Schauerte |
| 2002/0107553 A1 | 8/2002 | Hill et al. |
| 2002/0161415 A1 | 10/2002 | Cohen et al. |
| 2003/0040774 A1 | 2/2003 | Terry, Jr. et al. |
| 2003/0045914 A1 | 3/2003 | Cohen et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236557 A1 | 12/2003 | Whitehurst et al. |
| 2004/0048795 A1 | 3/2004 | Ivanova et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0215289 A1 | 10/2004 | Fukui |
| 2004/0243182 A1 | 12/2004 | Cohen et al. |
| 2004/0249416 A1 | 12/2004 | Yun et al. |
| 2005/0131467 A1 | 6/2005 | Boveja |
| 2005/0187584 A1 | 8/2005 | Denker et al. |

| | | |
|---|---|---|
| 2005/0222644 A1 | 10/2005 | Killian et al. |
| 2006/0015153 A1 | 1/2006 | Gliner et al. |
| 2006/0052831 A1 | 3/2006 | Fukui |
| 2006/0074450 A1 | 4/2006 | Boveja et al. |
| 2006/0129205 A1 | 6/2006 | Boveja et al. |

FOREIGN PATENT DOCUMENTS

| | | |
|---|---|---|
| WO | WO 01/10375 | 2/2000 |
| WO | WO 01/10432 A1 | 2/2001 |
| WO | WO 01/26729 A1 | 4/2001 |
| WO | WO 2002/087683 | 11/2002 |
| WO | WO 2003/018113 | 3/2003 |

OTHER PUBLICATIONS

A spiral nerve cuff electrode for peripheral nerve stimulation, by Gregory G. Naples, et al., IEEE Transactions on Biomedical Engineering, vol. 35, No. 11, Nov. 1988.

A nerve cuff technique for selective excitation of peripheral nerve trunk regions, by James D. Sweeney, et al., IEEE Transactions on Biomedical Engineering, vol. 37, No. 7, Jul. 1990.

"Generation of undirectionally propagated action potentials in a peripheral nerve by brief stimuli", by Van Den Honert, et al., 206 Science, pp. 1311-1312, Dec. 14, 1979.

"A technique for collision block of peripheral nerve: Frequency dependence" Van Den Honert, C., Mortimer, J. T.: MP-12, IEEE Transactions on Biomedical Engineering, 28:379-382, 1981.

"A nerve cuff design for selective activation and blocking of myelinated nerve fibers", D.M. Fitzpatrick, et al., Ann. Conf. Of the IEEE Engineering in Medicine and Biology Soc., vol. 13, No. 2, pp. 906, 1991.

"Orderly recruitment of motoneurons in an acute rabit model", N.J.M. Rijkhof, et al., Ann. Conf. Of the IEEE Eng., Medicine and Biology Soc., vol. 20, No. 5, pp. 2564, 1998.

"Orderly stimulation of skeletal muscle motor units with tripolar nerve cuff electrode", R. Bratta, et al., IEEE Transactions on Biomedical Engineering, vol. 36, No. 8, pp. 836; 1989.

M. Devor, "Pain NetWorks", Handbook of Brand Theory and Neural Networks, Ed. M.A. Arbib, MIT Press, pp. 698, 1998.

U.S. Appl. No. 09/824,682, entitled "Method and Apparatus for selective Control of Nerve fibers", filed Apr. 4, 2001.

http://www.bcm.tmc.edu/neurol/struct/epilep/epilepsy_vagus.html. May 31, 2001.

J.F. Cortese, "Vagus Nerve Stimulation for Control of Intractable Epileptic Seizures", available at http://www.science.wayne.edu/~bio340/StudentPages/cortese/, May 31, 2001.

Youhua Zhang, et al., "Optimal vertricular rate slowing during atrial fibrillation by feedback AV nodal-selective vagal stimulation", Am J. Physiol Heart Circ Physiol 282:H1102-H1110, 2002.

N.J.M. Rijkhoff et al., "Selective Stimulation of Small Diameter Nerve Fibers in a Mixed Bundle", Proceedings of the Annual Project Meeting Sensations/Neurons and Mid Term Review Meeting Neuros, Apr. 21-23, 1999.

M. Manfredi, "Differential Block of Conduction of larger fibers in peripheral nerve by direct current", Arch. Ital. Biol. 108:52-71, 1970.

Don W. Wallick, et al., "Selective AV nodal vagal stimulation improves hemodynamics during acute atrial fibrillation in dogs", Am J. Physiol Heart Circ Physiol, 281: H1490-H1497, 2001.

Masato Tsuboi et al., "Inotropic, chronotropic and dromotropic effects mediated via parasympathetic ganglia in the dog heart", Am J. Physiol Heart Circ Physiol, 279: H1201-H1207, 2000.

C.W. Chiou et al., "Efferent vagal innervation of the canine atria and sinus and atrioventricular nodes", Circulation, 1997; 95:2573.

P. Schauerte, et al, "Catheter stimulation of cariac parasympathetic nerves in humans", available at http://www.circulationaha.org, pp. 2430-2435, 2001.

M. Hirose, "Pituitary adenylate cyclase-activating polypeptide-27 causes a biphasic chronotropic effect and atrial fibrillation in autonomically decentralized, anesthetized dogs", The Journal of Pharmacology and Experimental Therapeutics, vol. 283, No. 2, pp. 478-487, 1997.

Carlson MD et al., "Selective stimulation of parasympathetic nerve fibers to the human sinoatrial node," Circuation 85:1311-1317 (1992).

Page PL et al., "Regional distribution of atrial electrical changes induced by stimulation of extracardiac and intracardiac neural elements," J Thorac Cardiovasc Surg. 109(2):377-88 (1995).

Furukawa Y et al., "Differential blocking effects of atropine and gallamine on negative chrontropic and dromotropic responses to vagus stimulation in anesthetized dogs," J Pharmacol Exp. Ther. 251(3):797-802 (1989).

Bluemel KM, "Parasympathetic postganglionic pathways to the sinoatrial node, " J Physiol. 259 (5 Pt 2): H1504-10 (1990).

Mazgalev TN, "AV Nodal Physiology," Heart Rhythm Society (www.hrsonline.org), no date.

Bibevski S et al. "Ganglionic Mechanisms Contribute to Diminished Vagal Control in Heart Failure," Circulation 99:2958-2963 (1999).

Garrigue S et al., "Post-ganglionic vagal stimulation of the atrioventricular node reduces ventricular rate during atrial fibrillation,"Pace 21(4), Part II, 878 (1998).

Chen SA et al., "Intracardiac stimulation of human parasympathetic nerve fibers induces negative dromotropic effects: implication with the lesions of radiofrequency catheter ablation," J Cardiovasc Electrophysiol. 9(3):245-52 (1998).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Waninger MS et al., "Electrophysiological control of ventricular rate during atrial fibrillation," Pace 23:1239-1244 (2000).

Goldberger JJ et al., "New technigue for vagal nerve stimulation," J Neurosci Methods. 91(1-2):1089-14 (1999).

Fang, et al., 1991. "Selective activation of small motor axons by quasitrapezoidal current pulses". IEEE Transactions on Biomedical Engineering 38: 168-174.

Stampfli, Robert, 1954. "Saltatory conduction in nerve". Physiol. Rev. 34: 101-112.

Deurloo, et al., (1998) "Transverse Tripolar Stimulation of Peripheral Nerve: a modeling study of spatial selectivity," *Med Biol Eng Comput*, 36(1): 66-74.

Goodall, et al., (1996) "Position-selctive Activation of Peripheral Nerve Fibers With a Cuff Electrode," *IEEE Trans Biomed Eng*, 43(8): 851-856.

Grill, et al., (1997) "Inversion of the Current-distance Relationship by Transient Depolarization," *IEEE Trans Biomed Eng*, 44(1): 1-9.

Martin, et al., (1983) "Phasic Effects of Repetitive Vagal Stimulation on Atrial Contraction," *Circ. Res.*, 52(6): 657-663.

Randall, (1977) "Neural Regulation of the Heart," Oxford University Press, 100-106.

Tarver, et al., (1992) "Clinical Experience with a Helical Bipolar Stimulating Lead, " *Pace* vol. 15, Oct., Part II.

Veraart, et al., (1993) "Selective Control of Muscle Activation with a Multipolar Nerve Cuff Electrode," *IEEE Trans Biomed Eng*, 40(7): 640-653.

Bilgutay, et al., (1968) "Vagal Tuning: a new concept in the treatment of supraventricular arrhythmias, angina pectoris, and heart failure," *J. Thoracic Cardiovas. Surg.*, 56(1): 71-82.

Jones, et al., (1998) "Activity of C Fibre Cardiac Vagal Efferents in Anaesthetized Cats and Rats," *Journal of Physiology*, 507.3: 869-880.

Office Action issued Mar. 27, 2007 during the prosecution of Applicants' U.S. Appl. No. 10/948,516.

Office Action, issued Oct. 27, 2009, in connection with U.S. Appl. No. 11/340,156, filed Jan. 25, 2006.

Office Action, issued Nov. 9, 2009, in connection with U.S. Appl. No. 11/064,446, filed Feb. 22, 2005.

Office Action issued Apr. 1, 2009 during the prosecution of Applicants' U.S. Appl. No. 11/359,266.

U.S. Appl. No. 60/263,834, entitled: Selected Blocking of Nerve Fibers, filed Jan. 25, 2001.

"Generation of undirectionally propagting action potentials using a monopolar electrode cuff". Annals of Biomedical Engineering, vol. 14, pp. 437-450, 1986, By Ira J. Ungar et al.

"An asymmetric two electrode cuff for generation of undirectionally propagated action potentials", IEEE Transactions on Biomedical Engineering, vol. BME-33, No. 6, Jun. 1986, By James D. Sweeney, et al.

Apr. 5, 2007 Office Action, issued by the U.S. Patent and Trademark Office, in connection with U.S. Appl. No. 10/488,334.

Apr. 25, 2008 Office Action, issued by the U.S. Patent and Trademark Office, in connection with U.S. Appl. No. 10/488,334.

Jones, et al., (1995) "Heart Rate Responses to Selective Stimulation of Cardiac Vagal C Fibers in Anaesthesized Cats, Rats, and Rabbits," *Journal of Physiology*, 489 1: 203-214.

* cited by examiner

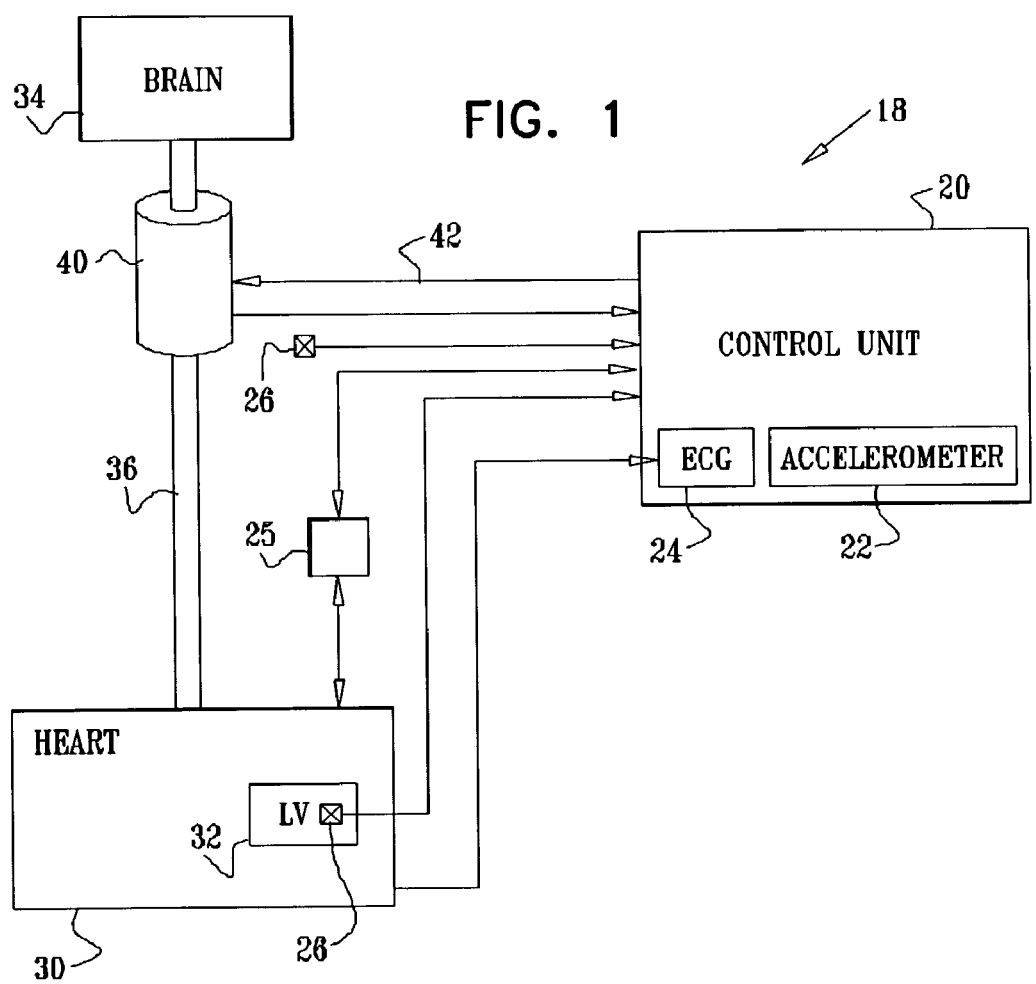

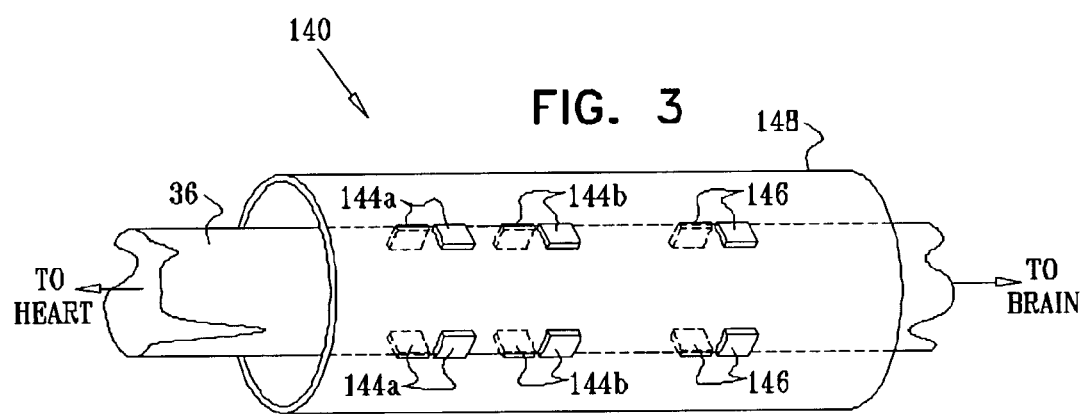

SELECTIVE NERVE FIBER STIMULATION FOR TREATING HEART CONDITIONS

CROSS-REFERENCE TO RELATED APPLICATIONS

The present patent application is a continuation-in-part of PCT Patent Application PCT/IL02/00068, filed Jan. 23, 2002, entitled, "Treatment of disorders by unidirectional nerve stimulation," which is a continuation-in-part of U.S. patent application Ser. No. 09/944,913, filed Aug. 31, 2001 now U.S. Pat. No. 6,684,105, entitled, "Treatment of disorders by unidirectional nerve stimulation." The '068 application and the '913 application are assigned to the assignee of the present patent application and are incorporated herein by reference.

This application is related to a U.S. patent application to Gross et al., filed on even date, entitled, "Electrode assembly for nerve control," which is assigned to the assignee of the present patent application and is incorporated herein by reference.

This application claims the benefit of U.S. Provisional Patent Application No. 60/383,157 to Ayal et al., filed May 23, 2002, entitled, "Inverse recruitment for autonomic nerve systems," which is assigned to the assignee of the present patent application and is incorporated herein by reference.

FIELD OF THE INVENTION

The present invention relates generally to treating patients by application of electrical signals to a selected nerve or nerve bundle, and specifically to methods and apparatus for stimulating the vagus nerve for treating heart conditions.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. When the vagus nerves fail to properly stimulate the heart, various arrhythmias may result, including tachycardia and atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including heart failure and atrial fibrillation. Heart failure is a cardiac condition characterized by a deficiency in the ability of the heart to pump blood throughout the body and/or to prevent blood from backing up in the lungs. Customary treatment of heart failure includes medication and lifestyle changes. It is often desirable to lower the heart rates of patients suffering from faster than normal heart rates. The effectiveness of beta blockers in treating heart disease is attributed in part to their heart-rate-lowering effect.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats.

PCT Patent Publication WO 01/26729 to Terry et al., which is incorporated herein by reference, describes techniques to increase cardiac output in patients suffering from heart failure. An implanted neurostimulator stimulates the vagus nerve in order to decrease the heart rate towards a target rate within the normal range. The vagal stimulation frequency is described as being automatically adjusted until the heart rate of the patient reaches the target rate. An activity sensor detects physical activity of the patient and adjusts the frequency of the stimulating pulses accordingly in order to elevate the heart rate during periods of physical activity.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart", Nervous Control of Vascular Function, Randall W C ed., Oxford University Press (1984)

Armour J A et al. eds., Neurocardiology, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," 237(3): H275-81 (1979)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken. Simultaneously, afferents from vagus and/or cardiac sympathetic nerves induce the brain to employ the brain's natural mechanisms of heart rhythm control.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagal nerves as well as the heart tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

U.S. Pat. No. 5,203,326 to Collins, which is incorporated herein by reference, describes a pacemaker which detects a cardiac abnormality and responds with electrical stimulation of the heart combined with vagal nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 5,199,428 to Obel et al., which is incorporated herein by reference, describes a cardiac pacemaker for detecting and treating myocardial ischemia. The device automatically stimulates the vagal nervous system as well as the heart tissue in a concerted fashion in order to decrease cardiac workload and thereby protect the myocardium.

A number of patents and articles describe other methods and devices for stimulating nerves to achieve a desired effect. Often these techniques include a design for an electrode or electrode cuff.

U.S. Pat. Nos. 4,608,985 to Crish et al. and 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

SUMMARY OF THE INVENTION

It is an object of some aspects of the present invention to provide apparatus and methods for treating and controlling a medical condition by application of electrical signals to a selected nerve or nerve bundle.

It is also an object of some aspects of the present invention to provide apparatus and methods for treating and controlling a medical condition by application of electrical signals to a selected nerve or nerve bundle while minimizing adverse side effects.

It is a further object of some aspects of the present invention to provide apparatus and methods for treating and controlling heart conditions by application of electrical signals to the vagus nerve, while minimizing adverse side effects.

It is still a further object of some aspects of the present invention to provide apparatus and methods for treating and controlling heart failure by reducing the heart rate and/or cardiac contractility.

It is yet a further object of some aspects of the present invention to provide apparatus and methods for treating and controlling heart failure by slowing the heart rate without inducing excessive variability in the induced heart rate.

It is an additional object of some aspects of the present invention to provide apparatus and methods for treating and controlling heart arrhythmias, such as fibrillation, atrial fibrillation or tachycardia, by slowing and/or stabilizing the heart rate, and/or reducing cardiac contractility.

It is yet an additional object of some aspects of the present invention to provide apparatus and methods for treating and controlling heart arrhythmias without inducing excessive variability in the induced heart rate.

It is still an additional object of some aspects of the present invention to provide apparatus and methods for treating and controlling heart conditions without the systemic side effects sometimes caused by pharmaceutical treatments of heart conditions.

In preferred embodiments of the present invention, apparatus for treating a heart condition comprises a multipolar electrode device that is applied to a portion of a vagus nerve that innervates the heart of a patient. Typically, the system is configured to treat heart failure and/or heart arrhythmia, such as atrial fibrillation or tachycardia. A control unit preferably drives the electrode device to (i) apply signals to induce the propagation of efferent action potentials towards the heart, and (ii) suppress artificially-induced afferent action potentials towards the brain, in order to minimize any unintended side effect of the signal application.

When inducing efferent action potentials towards the heart, the control unit preferably drives the electrode device to selectively recruit nerve fibers beginning with smaller-diameter fibers, and to recruit progressively larger-diameter fibers as the desired stimulation level increases. Preferably, in order to achieve this smallert-to-larger diameter fiber recruitment order, the control unit stimulates fibers essentially of all diameters using cathodic current from a central cathode, while simultaneously inhibiting fibers in a larger-to-smaller diameter order using anodal current ("efferent anodal current") from a set of one or more anodes placed between the central cathode and the edge of the electrode device closer to the heart ("the efferent anode set"). The amount of parasympathetic stimulation delivered to the heart is preferably increased by decreasing the number of fibers affected by the efferent anodal current, in a smaller-to-larger diameter order, e.g., by decreasing the amplitude or frequency of the efferent anodal current applied to the nerve.

The control unit preferably suppresses afferent action potentials induced by the cathodic current by inhibiting essentially all or a large fraction of fibers using anodal current ("afferent anodal current") from a second set of one or more anodes (the "afferent anode set"). The afferent anode set is preferably placed between the central cathode and the edge of the electrode device closer to the brain (the "afferent edge"), to block essentially all fibers from conveying signals in the direction of the brain during application of the afferent anodal current.

In some preferred embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set preferably comprises a plurality of anodes in order to minimize the virtual cathode effect in the direction of the brain.

Preferably, parasympathetic stimulation of the vagus nerve is applied responsive to one or more sensed physiological parameters or other parameters, such as heart rate, electrocardiogram (ECG), blood pressure, indicators of cardiac contractility, cardiac output, norepinephrine concentration, or motion of the patient. Preferably, stimulation is applied in a closed-loop system in order to achieve and maintain a desired heart rate responsive to one or more such sensed parameters.

In some preferred embodiments of the present invention, vagal stimulation is applied in a series of pulses. The application of the series of pulses in each cardiac cycle preferably commences after a variable delay after a detected R-wave, P-wave, or other feature of an ECG. The delay is preferably calculated in real time using a function, the inputs of which include one or more pre-programmed but updateable constants and one or more sensed parameters, such as the R-R interval between cardiac cycles and/or the P-R interval. Alternatively or additionally, a lookup table of delays is used to determine in real time the appropriate delay for each application of pulses, based on the one or more sensed parameters.

Advantageously, the techniques described herein generally enable relatively fine control of the level of stimulation of the vagus nerve, by imitating the natural physiological smaller-to-larger diameter recruitment order of nerve fibers. This an recruitment order allows improved and more natural control over the heart rate. Such fine control is particularly advantageous when applied in a closed-loop system, wherein such control results in smaller changes in heart rate and lower latencies in the control loop, which generally contribute to greater loop stability and reduced loop stabilization time. The use of a variable delay prior to application of pulses generally reduces the beat-to-beat variability of the heart rate sometimes experienced when using techniques having a constant ECG-based delay before application of pulses.

"Vagus nerve," and derivatives thereof, as used in the specification and the claims, is to be understood to include portions of the left vagus nerve, the right vagus nerve, and branches of the vagus nerve such as the superior cardiac nerve. Similarly, stimulation of the vagus nerve is described herein by way of illustration and not limitation, and it is to be understood that stimulation of other autonomic nerves, including nerves in the epicardial fat pads, for treatment of heart conditions or other conditions, is also included within the scope of the present invention.

"Heart failure," as used in the specification and the claims, is to be understood to include all forms of heart failure, including ischemic heart failure, nonischemic heart failure, and diastolic heart failure.

There is therefore provided, in accordance with a preferred embodiment of the present invention, apparatus for treating a heart condition of a subject, including:

an electrode device, adapted to be coupled to a vagus nerve of the subject; and a control unit, adapted to:

drive the electrode device to apply to the vagus nerve a stimulating current, which is capable of inducing action potentials in a therapeutic direction in a first set and a second set of nerve fibers of the vagus nerve, and drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

Preferably, the therapeutic direction is an efferent therapeutic direction towards a heart of the subject. Alternatively or additionally, the therapeutic direction is an afferent therapeutic direction towards a brain of the subject.

In a preferred embodiment, the control unit increases a number of action potentials traveling in the therapeutic direction by decreasing an amplitude of the applied inhibiting current, and/or decreases a number of action potentials traveling in the therapeutic direction by increasing an amplitude of the applied inhibiting current.

In a preferred embodiment, the heart condition includes heart failure and/or cardiac arrhythmia, and the apparatus is adapted to treat the heart condition.

Optionally, the apparatus includes an override, adapted to be used by the subject so as to influence the application by the electrode device of the stimulating and inhibiting currents.

In a preferred embodiment, the apparatus includes a pacemaker, and the control unit is adapted to drive the pacemaker to apply pacing pulses to a heart of the subject. Alternatively, the apparatus includes an implantable cardioverter defibrillator (ICD), and the control unit is adapted to drive the ICD to apply energy to a heart of the subject.

Preferably, the control unit is adapted to drive the electrode device to apply the stimulating current and/or the inhibiting current in a series of pulses.

In a preferred embodiment, the control unit receives an electrical signal from the electrode device, and drives the electrode device to regulate the stimulating and/or inhibiting current responsive to the electrical signal.

Preferably, the electrode device includes a cathode, adapted to apply the stimulating current, and a primary set of anodes, which applies the inhibiting current. Most preferably, the primary set of anodes includes a primary anode and a secondary anode, disposed so that the primary anode is located between the secondary anode and the cathode, and the secondary anode applies a current with an amplitude less than about one half an amplitude of a current applied by the primary anode.

Preferably, the control unit is adapted to drive the electrode device to apply the stimulating current so as to regulate a heart rate of the subject. Most preferably, the control unit is adapted to drive the electrode device to regulate an amplitude of the stimulating current so as to regulate the heart rate of the subject.

Alternatively or additionally, the control unit drives the electrode device to apply the inhibiting current so as to regulate a heart rate of the subject. In this case, the control unit preferably drives the electrode device to regulate an amplitude of the inhibiting current so as to regulate the heart rate of the subject.

Preferably, the control unit is adapted to drive the electrode device to apply the stimulating and inhibiting currents in a series of pulses. Most preferably, the control unit:

drives the electrode device to apply the stimulating and inhibiting currents in a series of about one to 20 pulses, configures the pulses to have a duration of between about one and three milliseconds, and/or drives the electrode device to apply the stimulating and inhibiting currents in the series of pulses over a period of between about one and about 200 milliseconds.

Preferably, the control unit drives the electrode device to apply the stimulating and inhibiting currents in the series of pulses so as to regulate a heart rate of the subject. Most preferably, the control unit regulates the number of pulses in the series of pulses so as to regulate the heart rate of the subject. Optionally, the control unit regulates a duration of each pulse so as to regulate the heart rate of the subject. Optionally, the control unit varies a length of a period of application of the series of pulses so as to regulate the heart rate of the subject.

In a preferred embodiment, the control unit drives the electrode device to apply to the vagus nerve a second inhibiting current, which is capable of inhibiting device-induced action potentials traveling in a non-therapeutic direction opposite the therapeutic direction in the first and second sets of nerve fibers.

Preferably, the control unit to drives the electrode device to apply the second inhibiting current to the vagus nerve at a primary and a secondary location, the primary location located between the secondary location and an application location of the stimulating current, and to apply at the secondary location a current with an amplitude less than about one half an amplitude of a current applied at the primary location.

In a preferred embodiment, the apparatus includes a sensor unit, and the control unit is adapted to receive at least one sensed parameter from the sensor unit, and to drive the electrode device to apply the stimulating and inhibiting currents responsive to the at least one sensed parameter.

Preferably, the control unit is adapted to determine a target heart rate of the subject responsive to the at least one sensed parameter, and the control unit is adapted to drive the electrode device to apply the stimulating and inhibiting currents so as to adjust a heart rate of the subject towards the target heart rate.

The sensor unit may include one or more of the following sensors, in which case the control unit receives the at least one sensed parameter from the following one or more sensors:
 a blood pressure sensor,
 a left ventricular pressure (LVP) sensor,
 an accelerometer (in which case, the at least one sensed parameter includes motion of the subject),
 a detector of norepinephrine concentration in the subject, and/or
 an impedance cardiography sensor.

Alternatively or additionally, the at least one sensed parameter includes an indicator of decreased cardiac contractility, an indicator of cardiac output, and/or an indicator of a time derivative of a LVP, and the control unit receives the indicator.

In a preferred embodiment, the sensor unit includes an electrocardiogram (ECG) monitor, the at least one sensed parameter includes an ECG value, and the control unit receives the at least one sensed parameter from the ECG monitor.

Preferably, the at least one sensed parameter includes an ECG reading indicative of a presence of arrhythmia, and the control unit is adapted to receive the at least one sensed parameter from the ECG monitor. Optionally, the at least one sensed parameter includes an indication of a heart rate of the subject, and the control unit is adapted to receive the indication of the heart rate. Further optionally, the at least one sensed parameter includes indications of a plurality of heart rates of the subject at a respective plurality of points in time, and the control unit is adapted to receive the at least one sensed parameter and to determine a measure of variability of heart rate responsive thereto.

In a preferred embodiment, the sensor unit is adapted to sense an initiation physiological parameter and a termination physiological parameter of the subject, and the control unit is adapted to drive the electrode device to apply the stimulating and inhibiting currents to the vagus nerve after a delay, to initiate the delay responsive to the sensing of the initiation physiological parameter, and to set a length of the delay responsive to the termination physiological parameter.

Preferably, the control unit is adapted to determine a target heart rate of the subject responsive to the at least one sensed parameter, and the control unit is adapted to set the delay so as to adjust the heart rate towards the target heart rate.

Optionally, the termination physiological parameter includes an atrioventricular (AV) delay of the subject, and the control unit is adapted to set the length of the delay responsive to the AV delay.

Preferably, the sensor unit includes an electrocardiogram (ECG) monitor, and the initiation physiological parameter includes a P-wave or R-wave of a cardiac cycle of the subject, and wherein the control unit is adapted to initiate the delay responsive to the sensing of the P-wave or R-wave, as the case may be. Preferably, the termination physiological parameter includes a difference in time between two features of an ECG signal recorded by the ECG monitor, such as an R-R interval between a sensing of an R-wave of a first cardiac cycle of the subject and a sensing of an R-wave of a next cardiac cycle of the subject, or a P-R interval between a sensing of a P-wave of a cardiac cycle of the subject and a sensing of an R-wave of the cardiac cycle, and the control unit sets the length of the delay responsive to the termination physiological parameter.

There is further provided, in accordance with a preferred embodiment of the present invention, apparatus for treating a heart condition of a subject, including:
 a cathode, adapted to apply to a vagus nerve of the subject a stimulating current which is capable of inducing action potentials in the vagus nerve; and
 a primary and a secondary anode, adapted to be disposed so that the primary anode is located between the secondary anode and the cathode, and adapted to apply to the vagus nerve respective primary and secondary inhibiting currents which are capable of inhibiting action potentials in the vagus nerve.

Preferably, the primary and secondary anodes are adapted to be placed between about 0.5 and about 2.0 millimeters apart from one another. Further preferably, the secondary anode is adapted to apply the secondary inhibiting current with an amplitude equal to between about 2 and about 5 milliamps. Still further preferably, the secondary anode is adapted to apply the secondary inhibiting current with an amplitude less than about one half an amplitude of the primary inhibiting current applied by the primary anode.

In a preferred embodiment, the primary anode, the secondary anode, and/or the cathode includes a ring electrode adapted to apply a generally uniform current around a circumference of the vagus nerve. Alternatively or additionally, the primary anode, the secondary anode, and/or the cathode includes a plurality of discrete primary anodes, adapted to be disposed at respective positions around an axis of the vagus nerve.

Optionally, the apparatus includes a tertiary anode, adapted to be disposed such that the secondary anode is between the tertiary anode and the primary anode.

Preferably, the electrode device includes an efferent edge, and the cathode is adapted to be disposed closer than the anodes to the efferent edge of the electrode device.

Preferably, the cathode and/or the anodes are adapted to apply the stimulating current so as to regulate a heart rate of the subject.

Optionally, the cathode includes a plurality of discrete cathodes, adapted to be disposed at respective positions around an axis of the vagus nerve, so as to selectively stimulate nerve fibers of the vagus nerve responsive to the positions of the nerve fibers in the vagus nerve.

Optionally, the apparatus includes a set of one or more blocking anodes, adapted to be disposed such that the cathode is between the set of blocking anodes and the primary anode, and adapted to apply to the vagus nerve a current which is capable of inhibiting action potentials propagating in the vagus nerve in a direction from the cathode towards the set of blocking anodes.

Preferably, the set of blocking anodes includes a first anode and a second anode, adapted to be disposed such that the first anode is located between the second anode and the cathode, and wherein the second anode is adapted to apply a current with an amplitude less than about one half an amplitude of a current applied by the first anode.

Preferably, the electrode device includes an afferent edge, wherein the cathode is adapted to be disposed closer than the anodes to the afferent edge of the electrode device.

Preferably, the apparatus includes a cuff, and an electrically-insulating element coupled to an inner portion of the cuff, and the primary anode and the cathode are adapted to be mounted in the cuff and separated from one another by the insulating element. Preferably, the primary and secondary anodes and the cathode are recessed in the cuff so as not to be in direct contact with the vagus nerve.

Preferably, the apparatus includes a control unit, adapted to drive the cathode and the anodes to apply the respective currents to the vagus nerve, so as to treat the subject.

Preferably, the cathode is adapted to apply the stimulating current and the anodes are adapted to apply the inhibiting current so as to regulate a heart rate of the subject. Optionally, the cathode is adapted to vary an amplitude of the applied stimulating current and the anodes are adapted to vary an amplitude of the applied inhibiting current so as to regulate a heart rate of the subject.

There is still further provided, in accordance with a preferred embodiment of the present invention, apparatus for treating a heart condition of a subject, including:

an electrode device, adapted to be coupled to a vagus nerve of the subject;

a sensor unit, adapted to sense an initiation physiological parameter and a termination physiological parameter of the subject; and a control unit, adapted to:

drive the electrode device to apply to the vagus nerve, after a delay, a current which is capable of inducing action potentials that propagate in the vagus nerve, initiate the delay responsive to the sensing of the initiation physiological parameter, and set a length of the delay responsive to the termination physiological parameter.

Optionally, the sensor unit includes a single sensor, adapted to sense the initiation physiological parameter and the termination physiological parameter.

The termination physiological parameter may include an atrioventricular (AV) delay of the subject, a respiration parameter of the subject, and the control unit is adapted to set the length of the delay responsive to the termination physiological parameter.

Preferably, the control unit is adapted to:

drive the electrode device to apply to the vagus nerve a stimulating current, which is capable of inducing action potentials in a therapeutic direction in a first set and a second set of nerve fibers of the vagus nerve, and drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

Optionally, the termination physiological parameter includes a blood pressure of the subject, and wherein the control unit is adapted to set the length of the delay responsive to the blood pressure.

Preferably, the sensor unit is adapted to sense a rate-setting parameter of the subject, wherein the rate-setting parameter includes a blood pressure of the subject, and wherein the control unit is adapted to receive the rate-setting parameter from the sensor unit and to drive the electrode device to apply the current responsive to the rate-setting parameter.

Optionally, the rate-setting parameter includes the initiation physiological parameter and/or the termination physiological parameter, and the control unit is adapted to drive the electrode device to apply the current responsive to the initiation physiological parameter so as to regulate the heart rate of the subject.

Preferably, the control unit is adapted to set the length of the delay so as to adjust the heart rate towards the target heart rate. Optionally, the control unit is adapted to access a lookup table of delays, and to set the length of the delay using the lookup table and responsive to the initiation and termination physiological parameters.

Preferably, the initiation physiological parameter includes a P-wave, R-wave, Q-wave, S-wave, or T-wave of a cardiac cycle of the subject, and wherein the control unit is adapted to initiate the delay responsive to the sensing of the cardiac wave.

Preferably, the termination physiological parameter includes a difference in time between two features of an ECG signal recorded by the ECG monitor, and the control unit is adapted to set the length of the delay responsive to the difference in time between the two features. The termination physiological parameter may include an R-R interval between a sensing of an R-wave of a first cardiac cycle of the subject and a sensing of an R-wave of a next cardiac cycle of the subject, and wherein the control unit is adapted to set the length of the delay responsive to the R-R interval. Alternatively or additionally, the termination physiological parameter includes an average of R-R intervals sensed for a number of cardiac cycles, and wherein the control unit is adapted to set the length of the delay responsive to the average of the R-R intervals.

Alternatively, the termination physiological parameter includes a P-R interval between a sensing of a P-wave of a cardiac cycle of the subject and a sensing of an R-wave of the cardiac cycle, and wherein the control unit is adapted to set the length of the delay responsive to the P-R interval. Alternatively or additionally, the termination physiological parameter includes an average of P-R intervals sensed for a number of cardiac cycles, and wherein the control unit is adapted to set the length of the delay responsive to the average of the P-R intervals.

There is also provided, in accordance with a preferred embodiment of the present invention, apparatus for treating a condition of a subject, including:

an electrode device, adapted to be coupled to an autonomic nerve of the subject; and a control unit, adapted to:

drive the electrode device to apply to the nerve a stimulating current, which is capable of inducing action potentials in a therapeutic direction in a first set and a second set of nerve fibers of the nerve, and drive the electrode device to apply to the nerve an inhibiting current, which is capable of inhibiting the induced action potentials traveling in the therapeutic direction in the second set of nerve fibers, the nerve fibers in the second set having generally larger diameters than the nerve fibers in the first set.

Preferably, the autonomic nerve includes one or more of the following:

a lacrimal nerve, a salivary nerve, a vagus nerve, a pelvic splanchnic nerve, a sympathetic nerve, and the control unit is adapted to drive the electrode device to apply the stimulating and inhibiting currents to the nerve.

Preferably, the control unit is adapted to drive the electrode device to apply the stimulating and inhibiting currents to the nerve so as to affect behavior of one of the following, so as to treat the condition:
a lung of the subject,
a stomach of the subject,
a pancreas of the subject,
a small intestine of the subject,
a liver of the subject,
a spleen of the subject,
a kidney of the subject,
a bladder of the subject,
a rectum of the subject,
a large intestine of the subject,
a reproductive organ of the subject, and/or
an adrenal gland of the subject.

There is additionally provided, in accordance with a preferred embodiment of the present invention, apparatus for treating a condition of a subject, including:
a cathode, adapted to apply to an autonomic nerve of the subject a stimulating current which is capable of inducing action potentials in the nerve; and
a primary and a secondary anode, adapted to be disposed so that the primary anode is located between the secondary anode and the cathode, and adapted to apply to the nerve respective primary and secondary inhibiting currents which are capable of inhibiting action potentials in the nerve.

There is yet additionally provided, in accordance with a preferred embodiment of the present invention, a method for treating a heart condition of a subject, including:
applying, to a vagus nerve of the subject, a stimulating current which is capable of inducing action potentials in a therapeutic direction in a first set and a second set of nerve fibers of the vagus nerve; and
applying to the vagus nerve an inhibiting current which is capable of inhibiting the induced action potentials traveling in the therapeutic direction in the second set of nerve fibers, the nerve fibers in the second set having generally larger diameters than the nerve fibers in the first set.

There is still additionally provided, in accordance with a preferred embodiment of the present invention, a method for treating a heart condition of a subject, including:
applying, to a vagus nerve of the subject, at a stimulation location, a stimulating current which is capable of inducing action potentials in the vagus nerve, so as to treat the subject; and
applying to the vagus nerve at a primary and a secondary location, the primary location located between the secondary location and the stimulation location, an inhibiting current which is capable of inhibiting action potentials in the vagus nerve.

There is further provided, in accordance with a preferred embodiment of the present invention, a method for treating a heart condition of a subject, including:
sensing an initiation physiological parameter and a termination physiological parameter of the subject;
setting a length of a delay period responsive to the termination physiological parameter;
initiating the delay period responsive to the initiation parameter; and
upon completion of the delay period, applying, to a vagus nerve of the subject, a current which is capable of inducing action potentials that propagate in the vagus nerve.

There is still further provided, in accordance with a preferred embodiment of the present invention, a method for treating a condition of a subject, including:

applying, to an autonomic nerve of the subject, a stimulating current which is capable of inducing action potentials in a therapeutic direction in a first set and a second set of nerve fibers of the nerve; and
applying to the nerve an inhibiting current which is capable of inhibiting the induced action potentials traveling in the therapeutic direction in the second set of nerve fibers, the nerve fibers in the second set having generally larger diameters than the nerve fibers in the first set.

There is also provided, in accordance with a preferred embodiment of the present invention, a method for treating a condition of a subject, including:
applying, to an autonomic nerve of the subject, at a stimulation location, a stimulating current which is capable of inducing action potentials in the nerve, so as to treat the subject; and
applying to the nerve at a primary and a secondary location, the primary location located between the secondary location and the stimulation location, an inhibiting current which is capable of inhibiting action potentials in the nerve.

The present invention will be more fully understood from the following detailed description of a preferred embodiment thereof, taken together with the drawings, in which:

BRIEF DESCRIPTION OF THE DRAWINGS

FIG. 1 is a block diagram that schematically illustrates a vagal stimulation system applied to a vagus nerve of a patient, in accordance with a preferred embodiment of the present invention;

FIG. 3 is a simplified perspective illustration of a multipolar point electrode device applied to a vagus nerve, in accordance with a preferred embodiment of the present invention;

DETAILED DESCRIPTION OF PREFERRED EMBODIMENTS

Figure 2A:
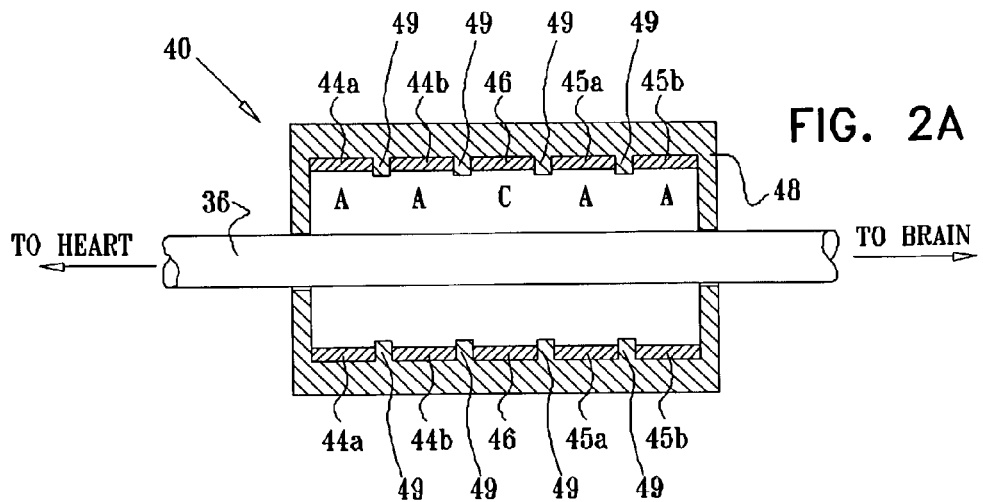
FIG. 2A is a simplified cross-sectional illustration of a multipolar electrode device applied to a vagus nerve, in accordance with a preferred embodiment of the present invention.

FIG. 1 is a block diagram that schematically illustrates a vagal stimulation system 18 comprising a multipolar electrode device 40, in accordance with a preferred embodiment of the present invention. Electrode device 40 is applied to a portion of a vagus nerve 36 that innervates a heart 30 of a patient. Typically, system 18 is utilized for treating a heart condition such as heart failure and/or cardiac arrhythmia. Vagal stimulation system 18 further comprises an implanted or external control unit 20, which typically communicates with electrode device 40 over a set of leads 42. Control unit 20 drives electrode device 40 to (i) apply signals to induce the propagation of efferent nerve impulses towards heart 30, and (ii) suppress artificially-induced afferent nerve impulses towards a brain 34 of the patient, in order to minimize unintended side effects of the signal application. The efferent nerve pulses in vagus nerve 36 are induced by electrode device 40 in order to regulate the heart rate of the patient.

For some applications, control unit 20 is adapted to receive feedback from one or more of the electrodes in electrode device 40, and to regulate the signals applied to the electrode device responsive thereto. For example, control unit 20 may analyze latencies of various peaks in a compound action potential (CAP) signal recorded by the electrodes, in order to determine a relative proportion of stimulated larger fibers (having faster conduction velocities) to smaller fibers (having slower conduction velocities). Alternatively or additionally, control unit 20 analyzes an area of the CAP, in order to determine an overall effect of the stimulation. Preferably, a relationship is determined between the effect on heart rate and the recorded CAP area and/or CAP latencies, and this relationship is used by the control unit to modulate the steps described in (i) and (ii) above. In a preferred embodiment, the feedback is received by electrodes other than those used to apply signals to the nerve.

Control unit 20 is preferably adapted to receive and analyze one or more sensed physiological parameters or other parameters of the patient, such as heart rate, electrocardiogram (ECG), blood pressure, indicators of decreased cardiac contractility, cardiac output, norepinephrine concentration, or motion of the patient. In order to receive these sensed parameters, control unit 20 may comprise, for example, an ECG monitor 24, connected to a site on the patient's body such as a heart 30, and/or the control unit may comprise an accelerometer 22 for detecting motion of the patient. Alternatively, ECG monitor 24 and/or accelerometer 22 comprise separate implanted devices placed external to control unit 20, and, optionally, external to the patient's body. Alternatively or additionally, control unit 20 receives signals from one or more physiological sensors 26, such as blood pressure sensors. Sensors 26 are preferably implanted in the patient, for example in a left ventricle 32 of heart 30. In a preferred embodiment, control unit 20 comprises or is coupled to an implanted device 25 for monitoring and correcting the heart rate, such as an implantable cardioverter defibrillator (ICD) or a pacemaker (e.g., a bi-ventricular or standard pacemaker). For example, implanted device 25 may be incorporated into a control loop executed by control unit 20, in order to increase the heart rate when the heart rate for any reason is too low.

FIG. 2A is a simplified cross-sectional illustration of a generally-cylindrical electrode device 40 applied to vagus nerve 36, in accordance with a preferred embodiment of the present invention. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Preferably, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

Cathodes 46 and anode sets 44 and 45 (collectively, "electrodes") are preferably mounted in an electrically-insulating cuff 48 and separated from one another by insulating elements such as protrusions 49 of the cuff. Preferably, the width of the electrodes is between about 0.5 and about 1 millimeter, or is equal to approximately one-half the radius of the vagus nerve. Further preferably, in order to achieve generally uniform field distributions of the currents generated by the electrodes, the electrodes are recessed so as not to come in direct contact with vagus nerve 36. Most preferably, the distance between the electrodes and the axis of the vagus nerve is between about 1.5 and 4 millimeters, and is greater than the closest distance from the ends of the protrusions to the axis of the vagus nerve. Preferably, protrusions 49 are relatively short (as shown). Most preferably, the distance between the ends of protrusions 49 and the center of the vagus nerve is between about 1.5 and 3 millimeters. (Generally, the radius of the vagus nerve is between about 1 and 2 millimeters.) Alternatively, for some applications, protrusions 49 are longer and/or the electrodes are placed closer to the vagus nerve in order to reduce the energy consumption of electrode device 40.

In a preferred embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In a preferred embodiment, anode 44a applies a current with an amplitude equal to about 2 to about 5 milliamps (typically one-third) of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is preferably positioned in cuff 48 to apply current at the location on vagus nerve 36 where the virtual cathode effect is maximally generated by anode 44b. For applications in which the blocking current through anode 44b is expected to vary substantially, efferent anode set 44 preferably comprises a plurality of virtual-cathode-inhibiting anodes 44a, one or more of which is activated at any time based on the expected magnitude and location of the virtual cathode effect.

Likewise, afferent anode set 45 preferably comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

As appropriate, techniques described herein are practiced in conjunction with methods and apparatus described in the above-cited U.S. patent application to Gross et al., filed on even date with the present patent application, entitled, "Electrode assembly for nerve control," which is assigned to the assignee of the present patent application and is incorporated herein by reference. Alternatively or additionally, techniques described herein are practiced in conjunction with methods and apparatus described in U.S. Provisional Patent Application No. 60/383,157 to Ayal et al., filed May 23, 2002, entitled, "Inverse recruitment for autonomic nerve systems," which is assigned to the assignee of the present patent application and is incorporated herein by reference.

Figure 2B:
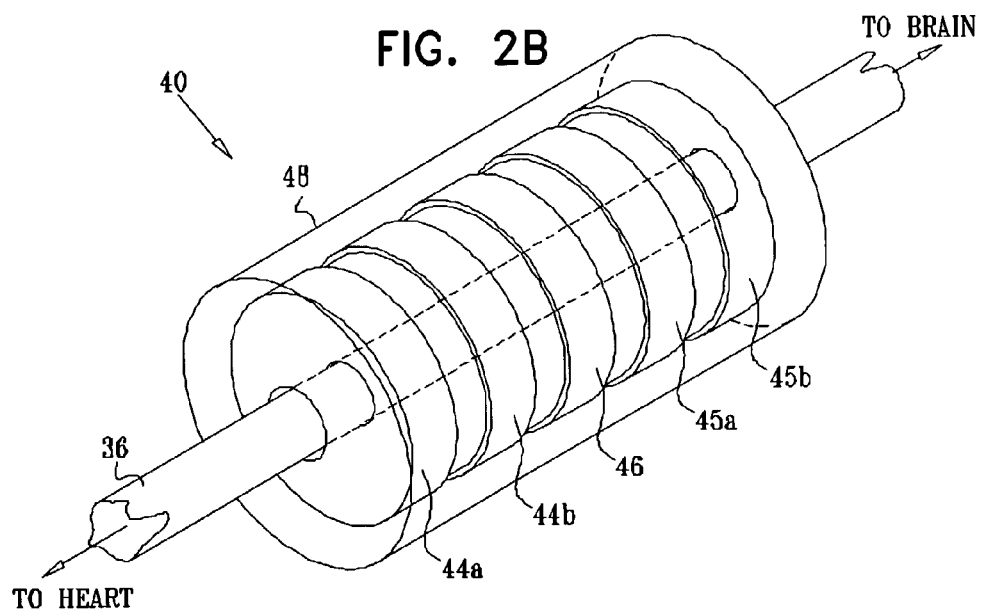
FIG. 2B is a simplified perspective illustration of the electrode device of FIG. 2A.

FIG. 2B is a simplified perspective illustration of electrode device 40. When applied to vagus nerve 36, electrode device 40 preferably encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes preferably comprise ring electrodes adapted to apply a generally uniform current around the circumference of the nerve, as best shown in FIG. 2B.

FIG. 3 is a simplified perspective illustration of a multipolar point electrode device 140 applied to vagus nerve 36, in accordance with a preferred embodiment of the present invention. In this embodiment, anodes 144a and 144b and a cathode 146 preferably comprise point electrodes (typically 2 to 100), fixed to an insulating cuff 148 and arranged around vagus nerve 36 so as to selectively stimulate nerve fibers according to their positions inside the nerve. In this case, techniques described in the above-cited articles by Grill et al., Goodall et al., and/or Veraart et al. are preferably used. The point electrodes preferably have a surface area between about 0.01 mm2 and 1 mm2. In some applications, the point electrodes are in contact with vagus nerve 36, as shown, while in other applications the point electrodes are recessed in cuff 148, so as not to come in direct contact with vagus nerve 36, similar to the recessed ring electrode arrangement described above with reference to FIG. 2A. For some applications, one or more of the electrodes, such as cathode 146 or anode 144a, comprise a ring electrode, as described with reference to FIG. 2B, such that electrode device 140 comprises both ring electrode(s) and point electrodes. Additionally, electrode device 40 optionally comprises an afferent anode set (positioned like anodes 45a and 45b in FIG. 2A), the anodes of which comprise point electrodes and/or ring electrodes.

Alternatively, ordinary, non-cuff electrodes are used, such as when the electrodes are placed on the epicardial fat pads instead of on the vagus nerve.

Figure 4:
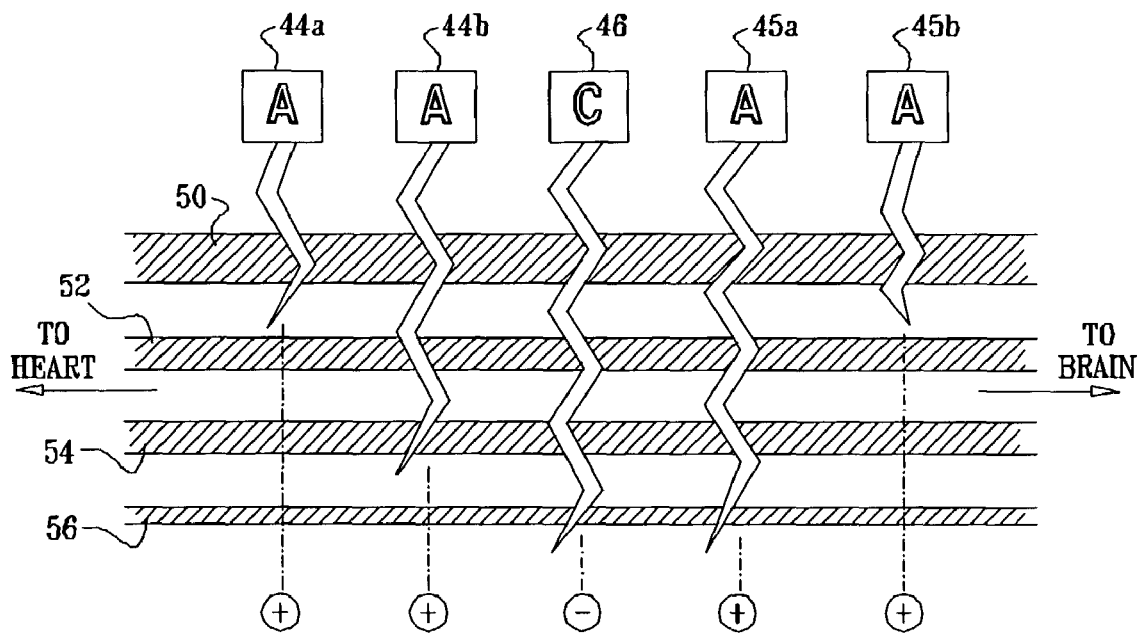
FIG. 4 is a conceptual illustration of the application of current to a vagus nerve, in accordance with a preferred embodiment of the present invention.

FIG. 4 is a conceptual illustration of the application of current to vagus nerve 36 in order to achieve smaller-to-larger diameter fiber recruitment, in accordance with a preferred embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Preferably, in order to achieve this recruitment order, the control unit stimulates fibers essentially of all diameters using cathodic current from cathode 46, while simultaneously inhibiting fibers in a larger-to-smaller diameter order using efferent anodal current from efferent anode set 44. For example, FIG. 4 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. In addition, for any given number of fibers stimulated (and not blocked), the amount of stimulation delivered to the heart can be increased by increasing the amplitude and/or frequency of the current applied to vagus nerve 36.

In order to suppress artificially-induced afferent action potentials from traveling towards the brain in response to the cathodic stimulation, control unit 20 preferably drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In a preferred embodiment of the present invention, stimulation of the vagus nerve is applied responsive to one or more sensed parameters. Control unit 20 is preferably configured to commence or halt stimulation, or to vary the amount and/or timing of stimulation in order to achieve a desired target heart rate, typically based on configuration values and on parameters including one or more of the following:

- Heart rate—the control unit can be configured to drive electrode device 40 to stimulate the vagus nerve only when the heart rate exceeds a certain value.
- ECG readings—the control unit can be configured to drive electrode device 40 to stimulate the vagus nerve based on certain ECG readings, such as readings indicative of designated forms of arrhythmia. Additionally, ECG readings are preferably used for achieving a desire heart rate, as described below with reference to FIG. 5.
- Blood pressure—the control unit can be configured to regulate the current applied by electrode device 40 to the vagus nerve when blood pressure exceeds a certain threshold or falls below a certain threshold.
- Indicators of decreased cardiac contractility—these indicators include left ventricular pressure (LVP). When LVP and/or d(LVP)/dt exceeds a certain threshold or falls below a certain threshold, control unit 20 can drive electrode device 40 to regulate the current applied by electrode device 40 to the vagus nerve.
- Motion of the patient—the control unit can be configured to interpret motion of the patient as an indicator of increased exertion by the patient, and appropriately reduce parasympathetic stimulation of the heart in order to allow the heart to naturally increase its rate.
- Heart rate variability—the control unit can be configured to drive electrode device 40 to stimulate the vagus nerve based on heart rate variability, which is preferably calculated based on certain ECG readings.
- Norepinephrine concentration—the control unit can be configured to drive electrode device 40 to stimulate the vagus nerve based on norepinephrine concentration.
- Cardiac output—the control unit can be configured to drive electrode device 40 to stimulate the vagus nerve based on cardiac output, which is preferably determined using impedance cardiography.

The parameters and behaviors included in this list are for illustrative purposes only, and other possible parameters and/or behaviors will readily present themselves to those skilled in the art, having read the disclosure of the present patent application.

In embodiments of the present invention in which vagal stimulation system 18 comprises implanted device 25 for monitoring and correcting the heart rate, control unit 20 preferably uses measured parameters received from device 25 as additional inputs for determining the level and/or type of stimulation to apply. Control unit 20 preferably coordinates its behavior with the behavior of device 25. Control unit 20 and device 25 preferably share sensors 26 in order to avoid redundancy in the combined system.

Optionally, vagal stimulation system 18 comprises a patient override, such as a switch that can be activated by the patient using an external magnet. The override preferably can be used by the patient to activate vagal stimulation, for example in the event of arrhythmia apparently undetected by the system, or to deactivate vagal stimulation, for example in the event of apparently undetected physical exertion.

Figure 5:
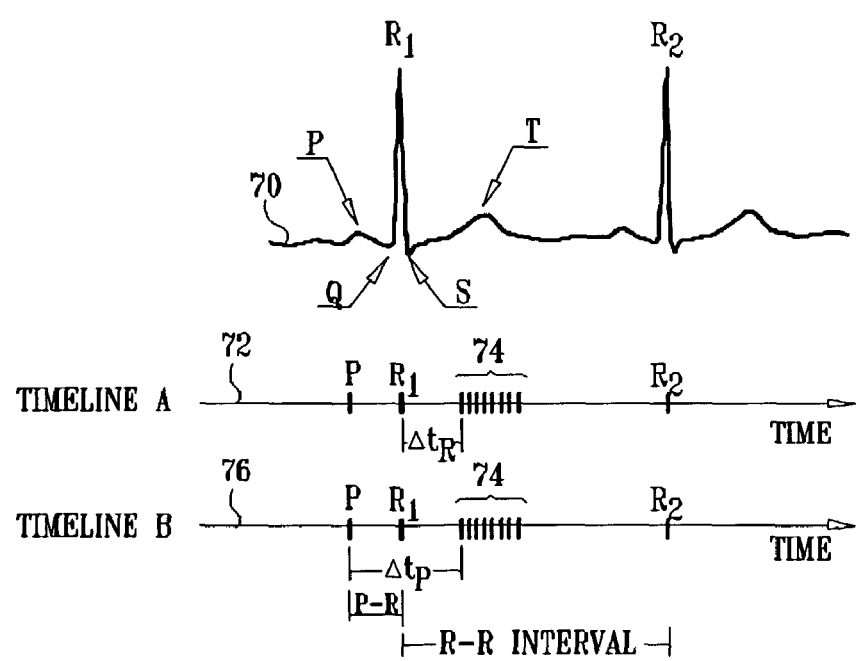
FIG. 5 is a simplified illustration of an electrocardiogram (ECG) recording and of example timelines showing the timing of the application of a series of stimulation pulses, in accordance with a preferred embodiment of the present invention.

FIG. 5 is a simplified illustration of an ECG recording 70 and example timelines 72 and 76 showing the timing of the application of a series of stimulation pulses 74, in accordance with a preferred embodiment of the present invention. Stimulation is preferably applied to vagus nerve 36 in a closed-loop system in order to achieve and maintain the desired target heart rate, determined as described above. Precise graded slowing of the heart beat is preferably achieved by varying the number of nerve fibers stimulated, in a smaller-to-larger diameter order, and/or the intensity of vagus nerve stimulation. Stimulation with blocking, as described herein, is preferably applied during each cardiac cycle in a series of pulses 74, preferably containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

To apply the closed-loop system, preferably the target heart rate is expressed as a ventricular R-R interval (shown as the interval between $R_1$ and $R_2$ in FIG. 5). The actual R-R interval is measured in real time and compared with the target R-R interval. The difference between the two intervals is defined as a control error. Control unit 20 calculates the change in stimulation necessary to move the actual R-R towards the target R-R, and drives electrode device 40 to apply the new calculated stimulation. Intermittently, e.g., every 1, 10, or 100 beats, measured R-R intervals or average R-R intervals are evaluated, and stimulation of the vagus nerve is modified accordingly.

The delay before applying pulse series 74 in each cardiac cycle influences the R-R interval achieved at any given level of stimulation. This delay can be measured from a number of sensed physiological parameters ("initiation physiological parameters"), including sensed points in the cardiac cycle, including P-, Q-, R-, S- and T-waves. Preferably the delay is measured from the P-wave, which indicates atrial contraction. Alternatively, the delay is measured from the R-wave, particularly when the P-wave is not easily detected. Timeline A 72 and Timeline B 76 show the delays, $t_R$ and $t_P$ measured from R and P, respectively.

When a closed-loop system is used with a constant t, a desired target R-R interval can be achieved, but a substantial R-R interval variability on a beat-to-beat basis often occurs, as described in Zhang Y et al., cited above. The techniques described herein, by varying t in real time (that is, using t as a controlled parameter), rather than using a constant t, generally substantially reduce this R-R interval variability.

Preferably, t from either R or P is calculated in real time using a function, the inputs of which include one or more numeric parameters and one or more ECG values or other physiological values ("termination physiological parameters") measured in real time. The termination physiological parameters determine how long the delay t will continue before pulse series 74 is begun. The values of the numeric parameters and which physiological inputs to use are preferably determined during a calibration procedure, as described below, or may be based on the particular heart condition and/or medical history of the patient being treated.

For example, t may be measured from R or P, as shown in timeline A 72 and timeline B 76, respectively, and the function may take the form of:

$$t=C+K*f(R\text{-}R \text{ interval}, P\text{-}R \text{ interval}),$$

wherein C and K are constants optimized to minimize R-R interval variability, and the R-R interval and/or P-R interval are inputs to the function. Alternatively or additionally, the function includes as inputs other ECG values and/or sensed physiological parameters, such as atrioventricular (AV) delay, blood pressure, or respiration. For some applications, the function includes other types of linear and non-linear relationships, such as exponentials or differentials.

Typically, the function uses the R-R or P-R interval, or other sensed parameters, that were measured in the previous cardiac cycle, in order to maximize responsiveness of the function to real-time changes in heart rate. Alternatively, the interval or other sensed parameters are calculated as a running average of intervals or parameters measured during a certain number of previous heart cycles, in order to smooth the variability of t from beat to beat.

In a preferred embodiment, t is obtained in real time from a lookup table, the inputs to which include one or more ECG or other physiological values. The lookup table is typically either populated during a calibration procedure, or with fixed values for a particular heart condition.

To facilitate the above process, a calibration procedure is preferably performed. This procedure is typically performed by a physician for an individual patient prior to or soon after installation of vagal stimulation system 18, or, alternatively or additionally, by or on behalf of the manufacturer of the system prior to its sale. During calibration for an individual patient, the physician preferably determines suitable parameters for real-time determination of t by recording ECGs of the patient under different levels of heart stress while applying stimulation with a range of values of t.

In a preferred embodiment, vagal stimulation system 18 is further configured to apply stimulation responsive to pre-set time parameters, such as intermittently, constantly, or based on the time of day.

Optionally, the stimulation applied by vagal stimulation system 18 is applied in conjunction with or separately from stimulation of sympathetic nerves innervating the heart. Such sympathetic stimulation can be applied using techniques of smaller-to-larger diameter fiber recruitment, as described herein, or other nerve stimulation techniques known in the art.

Alternatively or additionally, the techniques of smaller-to-larger diameter fiber recruitment and t control are applied in conjunction with methods and apparatus described in one or more of the patents, patent applications, articles and books cited herein.

Although preferred embodiments of the present invention are described herein with respect to treating heart conditions, it is to be understood that the scope of the present invention includes utilizing the techniques described herein to controllably stimulate the vagus nerve to facilitate other treatments, e.g., to treat depression, epilepsy, spasticity, obesity, syncope, brain disorders, gastrointestinal tract disorders, renal disorders, pancreatic disorders, or lung disorders. In particular, the techniques described herein may be performed in combination with other techniques, which are well known in the art or which are described in the references cited herein, that stimulate the vagus nerve in order to achieve a desired therapeutic end.

For some applications, techniques described herein are used to apply controlled stimulation to one or more of the following: the lacrimal nerve, the salivary nerve, the vagus nerve, the pelvic splanchnic nerve, or one or more sympathetic or parasympathetic autonomic nerves. Such controlled stimulation may be used, for example, to regulate or treat a condition of the lung, heart, stomach, pancreas, small intestine, liver, spleen, kidney, bladder, rectum, large intestine, reproductive organs, or adrenal gland.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a condition of a subject, comprising:
   an electrode device, configured to be coupled to a nerve of the subject;
   a sensor configured to sense at least one feature of cardiac activity of the subject; and
   a control unit, configured to:
      drive the electrode device to apply to the nerve a stimulating current, which is configured to induce action potentials in (i) a first set of nerve fibers of the nerve, and (ii) a second set of nerve fibers of the nerve having generally larger diameters than the nerve fibers in the first set,
      drive the electrode device to apply to the nerve an inhibiting current, which is configured to inhibit the induced action potentials in the second set of nerve fibers but not in the first set of fibers,
      responsively to the at least one sensed feature of cardiac activity of the subject, configure at least one current selected from the group consisting of: the stimulating current, and the inhibiting current, and
      regulate a heart rate of the subject by:
         driving the electrode device to apply the stimulating and inhibiting currents in each of a plurality of cardiac cycles of the subject in respective series of pulses, each of which pulse series is applied after a delay from a sensed point in the cardiac cycle, and varying a number of pulses applied per cardiac cycle and a length of a period of application of the respective series of pulses.

2. Apparatus according to claim 1, wherein the control unit is configured to:
   drive the electrode device to configure the stimulating current to induce the action potentials in an efferent therapeutic direction towards a heart of the subject, in the first and the second set of nerve fibers, and
   drive the electrode device to configure the inhibiting current to inhibit the induced action potentials traveling in the efferent therapeutic direction in the second set of nerve fibers.

3. Apparatus according to claim 1, wherein the control unit is configured to increase a number of action potentials traveling in the nerve by decreasing an amplitude of the applied inhibiting current.

4. Apparatus according to claim 1, wherein the control unit is configured to decrease a number of action potentials traveling in the nerve by increasing an amplitude of the applied inhibiting current.

5. Apparatus according to claim 1, wherein the condition includes a heart condition of the subject, and wherein the apparatus is configured to treat the heart condition.

6. Apparatus according to claim 5, wherein the heart condition includes heart failure, and the apparatus is configured to treat the heart failure.

7. Apparatus according to claim 5, wherein the heart condition includes cardiac arrhythmia, and the apparatus is configured to treat the cardiac arrhythmia.

8. Apparatus according to claim 1, comprising an override, configured to be used by the subject so as to influence the application by the electrode device of the stimulating and inhibiting currents.

9. Apparatus according to claim 1, comprising a pacemaker, wherein the control unit is configured to drive the pacemaker to apply pacing pulses to a heart of the subject.

10. Apparatus according to claim 1, comprising an implantable cardioverter defibrillator (ICD), wherein the control unit is configured to drive the ICD to apply energy to a heart of the subject.

11. Apparatus according to claim 1, wherein the sensor is configured to receive an electrical signal from the electrode device, and to sense the at least one feature of cardiac activity responsively to the electrical signal.

12. Apparatus according to claim 1, wherein the electrode device comprises a cathode and a primary set of anodes, and wherein the control unit is configured to drive the cathode to apply the stimulating current, and to drive the primary set of anodes to apply the inhibiting current.

13. Apparatus according to claim 1, wherein the control unit is configured to configure each of the series of pulses to include about one to 20 pulses.

14. Apparatus according to claim 1, wherein the control unit is configured to drive the electrode device to configure at least one of the pulses to have a duration of between about one and three milliseconds.

15. Apparatus according to claim 1, wherein the control unit is configured to drive the electrode device to apply the stimulating and inhibiting currents in each of the series of pulses over a period of between about one and about 200 milliseconds.

16. Apparatus according to claim 1, wherein the control unit is configured to:
   configure the stimulating current to induce the action potentials to travel in a therapeutic direction, and the inhibiting current to inhibit the induced action potentials traveling in the therapeutic direction, and
   drive the electrode device to apply to the nerve a second inhibiting current, which is capable of inhibiting device-induced action potentials traveling in a non-therapeutic direction opposite the therapeutic direction in the first and second sets of nerve fibers.

17. Apparatus according to claim 1, wherein the sensor comprises an electrocardiogram (ECG) monitor, wherein the at least one sensed feature of cardiac activity includes a feature of an ECG and wherein the sensor is configured to sense the feature of the ECG.

18. Apparatus according to claim 17, wherein the at least one sensed feature of cardiac activity includes an ECG reading indicative of a presence of arrhythmia, and wherein the sensor is configured to sense the ECG reading indicative of the presence of the arrhythmia.

19. Apparatus according to claim 1, wherein the at least one sensed feature of cardiac activity includes a heart rate of the subject, and wherein the sensor is configured to sense the heart rate.

20. Apparatus according to claim 19, wherein the at least one sensed feature of cardiac activity includes indications of a plurality of heart rates of the subject at a respective plurality of points in time, and wherein the control unit is configured to receive the indications of the plurality of heart rates and to determine a measure of variability of heart rate responsive thereto.

21. Apparatus according to claim 1, wherein the nerve includes a vagus nerve of the subject, and wherein the electrode device is configured to be coupled to the vagus nerve.

22. Apparatus according to claim 1, wherein the sensor comprises a sensor of cardiac output, and wherein the control unit is configured to configure the at least one selected current and regulate the heart rate responsively to the sensed cardiac output.

* * * * *